(12) United States Patent
Ascheman et al.

(10) Patent No.: US 6,981,403 B2
(45) Date of Patent: Jan. 3, 2006

(54) METHOD AND APPARATUS FOR MEASURING GAS TRANSMISSION RATES OF DEFORMABLE OR BRITTLE MATERIALS

(75) Inventors: Timothy Alan Ascheman, Ramsey, MN (US); Daniel W. Mayer, Wyoming, MN (US)

(73) Assignee: Mocon, Inc., Minneapolis, MN (US)

( * ) Notice: Subject to any disclaimer, the term of this patent is extended or adjusted under 35 U.S.C. 154(b) by 49 days.

(21) Appl. No.: 10/698,608

(22) Filed: Oct. 31, 2003

(65) Prior Publication Data

US 2005/0092068 A1    May 5, 2005

(51) Int. Cl.
*G01N 15/08*    (2006.01)
(52) U.S. Cl. ......................................................... 73/38
(58) Field of Classification Search .................. 73/38
See application file for complete search history.

(56) References Cited

U.S. PATENT DOCUMENTS

| | | | | |
|---|---|---|---|---|
| 3,926,561 A | * | 12/1975 | Lucero | .................... 436/178 |
| 4,464,927 A | * | 8/1984 | Reid | ............................. 73/38 |
| 5,817,924 A | * | 10/1998 | Tuomela et al. | ............... 73/38 |
| 5,837,888 A | | 11/1998 | Mayer et al. | .................. 73/38 |
| 6,119,506 A | * | 9/2000 | Gibson et al. | ................ 73/38 |
| 6,450,009 B1 | * | 9/2002 | Hartikainen et al. | ............ 73/38 |
| 6,640,615 B1 | * | 11/2003 | Morrow | ........................ 73/38 |

FOREIGN PATENT DOCUMENTS

JP        62-119433     *   5/1987

* cited by examiner

*Primary Examiner*—Daniel S. Larkin
(74) *Attorney, Agent, or Firm*—Sherrill Law Offices, PLLC

(57) ABSTRACT

Provided are an apparatus and a method for measuring gas transmission rates and nanoleaks of deformable and brittle materials. The apparatus includes a test chamber having an upper and lower diffusion cells that when closed form a chamber wall seal, a gas inlet and a gas outlet in fluid communication with the lower diffusion cell, the upper diffusion cell being fluidly connected to a high-vacuum mass spectrometer. The method of measuring gas transmission rates and nanoleaks includes placing a sealed package containing the test gas in the lower diffusion cell, closing the upper and lower diffusion cells, flushing the lower diffusion cell with a source of a second gas other than the test gas, closing off the source of the second gas; and measuring the leak rate of the sealed package.

1 Claim, 5 Drawing Sheets

METHOD AND APPARATUS FOR MEASURING GAS TRANSMISSION RATES OF DEFORMABLE OR BRITTLE MATERIALS

BACKGROUND OF THE INVENTION

1. Field of the Invention

The present invention relates to an apparatus and method for measuring the transmission rate and nanoleaks of a gas through a test material. In particular, the invention relates to an apparatus and method for measuring the gas transmission rates of brittle and deformable materials.

2. Description of the Related Art

Mass spectrometers use the difference in mass-to-charge ratio (m/e) of ionized atoms or molecules to separate them from each other. Mass spectrometry is therefore useful for quantitation of atoms or molecules and also for determining chemical and structural information about molecules. The general operation of a mass spectrometer is (i) create gas-phase ions; (ii) separate the ions in space or time based on their mass-to-charge ratio; and (iii) measure the quantity of ions of each mass-to-charge ratio. In general a mass spectrometer consists of an ion source, a mass-selective analyzer, and an ion detector. Because mass spectrometers create and manipulate gas-phase ions, they operate in a high-vacuum system.

The use of a mass spectrometer for measuring gas transmission rates of test materials is known. The necessity of calibrating a mass spectrometer prior to use is also known. In some cases, a mass spectrometer will be "tuned" to measure a particular gas. This results in very precise, accurate measurements of the gas that would otherwise not be possible. Mass spectrometers that are tuned to a particular gas may be used when the gas to be measured is present in very low concentrations or when the test material has a very low gas transmission rate making the gas difficult to measure without a "tuned" mass spectrometer. One drawback of this method, especially when measuring the gas transmission rate of deformable and brittle materials, is that mass spectrometers operate in high-vacuum systems, as noted previously.

When measuring the gas transmission rates of deformable and/or brittle test materials, the exposure of the test material to vacuum conditions may result in false positives, or in other words transmission rates and nanoleaks (caused by flexing of materials) in excess of actual values. Brittle materials are those which manifest fractures upon being subjected to stress without appreciable prior plastic deformation. Deformable materials are those which exhibit alterations in shape, dimensions, thickness, etc., caused by stress and/or expansion or contraction of the material. Consequently for example, when a test material is elastomeric in nature the high-vacuum system of the mass spectrometer may stretch and expand the material to a point that results in an increase in the permeability of the material. As a result gas transmission rates across the test material may be calculated as being higher than the actual transmission rate. Further, if the test material is brittle, as in the case of certain epoxies, direct exposure to high-vacuum conditions may cause the test material to fracture, One method of testing epoxies is to embed them in a metal holding plate. The plate contains machine-drilled holes and the epoxy test material is placed in the holes. The plate is then placed in a gas transmission test chamber similar to that depicted in FIG. 1. The brittle epoxy may fracture and/or delaminate from the metal plate as a result of the high-vacuum conditions in the upper test chamber. This phenomena causes leakage of the test gas through the fractures and around the junctures where delamination occurs, which in turn results in transmission rates in excess of the actual gas transmission rate of the test epoxy material.

It would, therefore, be advantageous to provide a process for measuring the rate of transmission of a gas through deformable and brittle test materials, wherein the measurement process can be very accurately determined and the measurement setup can be readily and conveniently constructed. It would also be an advantage to provide for a process to test the gas transmission rates of deformable materials so that such materials would not be subjected to vacuum conditions that could potentially result in increased permeability due to the expansion of the test material. It would also be an advantage to provide for a process to determine the gas transmission rates of brittle materials and materials that may be susceptible to delamination so that the brittle materials would not fracture and the materials susceptible to delamination would not delaminate. It would also be an advantage to provide for a process and apparatus for measuring the transmission rate and nanoleaks of a gas through a test material, e.g. sealed packages, air bladders of athletic shoes, computer hard drives, etc., with the test gas inside, that could easily be adapted to the quality assurance laboratory of a manufacturing plant so that data could be collected from production samples to assess quality assurance parameters. The present invention accomplishes this purpose to great advantage and provides a significant advance in the arts.

SUMMARY OF THE INVENTION

A process for measuring the gas transmission rate through a deformable or brittle test material is provided. The process includes providing a test chamber including an upper diffusion cell and a lower diffusion cell that when closed form a chamber wall seal, a gas inlet and a gas outlet in fluid communication with the lower diffusion cell and a mass spectrometer in communication with the upper diffusion cell; selecting a guard material of a known type; positioning said guard material between the lower diffusion cell and the upper diffusion cell; placing a support grid over said guard material so that it is immediately adjacent the upper diffusion cell; closing the upper and lower diffusion cells to form a chamber wall seal; providing through said gas inlet a source of a test gas and exhausting said test gas through said gas outlet; operating the mass spectrometer such that the upper diffusion cell is subjected to high-vacuum conditions; measuring the gas transmission rate of the guard material; opening the upper and lower diffusion cells of the test chamber to remove the guard material and position a test material sample between the upper diffusion cell and the lower diffusion cell; placing the guard material over the test material sample; placing the support grid over the guard material and immediately adjacent the upper diffusion cell; closing the upper and lower diffusion cells; providing through said gas inlet a source of a second gas and exhausting said second gas through said gas outlet; operating the mass spectrometer such that the upper diffusion cell is subject to high-vacuum conditions; calculating the leak rate of the chamber wall seals; maintaining the positions of the support grid, guard material and test material sample and providing through said gas inlet into said lower diffusion cell a source of said test gas and exhausting said test gas through said gas outlet; operating the mass spectrometer such that the upper diffusion cell is subjected to high-vacuum conditions; measuring the combined gas transmission rate of the guard material and the test material sample.

The gas transmission rate of the test material sample ($TR_{TMS}$) may be calculated from the following equation:

$TR_1$ = Transmission rate of Guard Material $TR_2$ = Transmission rate of Chamber Wall Seals $TR_3$ = Transmission rate of Guard Material and Test Material Sample $$\frac{1}{(TR_3 - TR_2)} - \frac{1}{TR_1} = \frac{1}{TR_{TMS}}$$

Solving for $TR_{TMS}$ $$TR_{TMS} = \frac{(TR_3 - TR_2)(TR_1)}{(TR_1) - (TR_3 - TR_2)}$$

When the test gas is not present in air, the leak rate of the chamber wall seals ($TR_2$) will be negligible, and will drop out of the equation. In such a case, the test for $TR_2$ can be eliminated and the equation simplifies to:

$$\frac{1}{TR_3} - \frac{1}{TR_1} = \frac{1}{TR_{TMS}}$$

Solving for $TR_{TMS}$ $$\frac{(TR_3)(TR_1)}{TR_1 - TR_3} = TR_{TMS}$$

Further, when the gas transmission rate of the guard material is about one hundred times greater than the transmission rate of the test material, $TR_1$ will dropout of the equation and the equation becomes:

$$\frac{1}{TR_3} = \frac{1}{TR_{TMS}}$$

It is a principal object of the present invention to provide a process for measuring the gas transmission rate of a particular and selected material, the material being brittle or deformable.

It is a further object of the present invention to provide a process for measuring transmission rates through brittle or deformable materials, according to a process that is easily and readily implemented especially in a manufacturing setting.

It is a further object of the present invention to provide an apparatus and process for measure the gas transmission rate of a test gas inside of a sealed package.

It is a further object and advantage of the present invention to provide a process for measuring gas transmission rates to a high degree of accuracy.

The foregoing and other objects and advantages will become apparent from the following specification and claims and with reference to the appended drawings.

DESCRIPTION OF THE PREFERRED EMBODIMENTS

Figure 1:
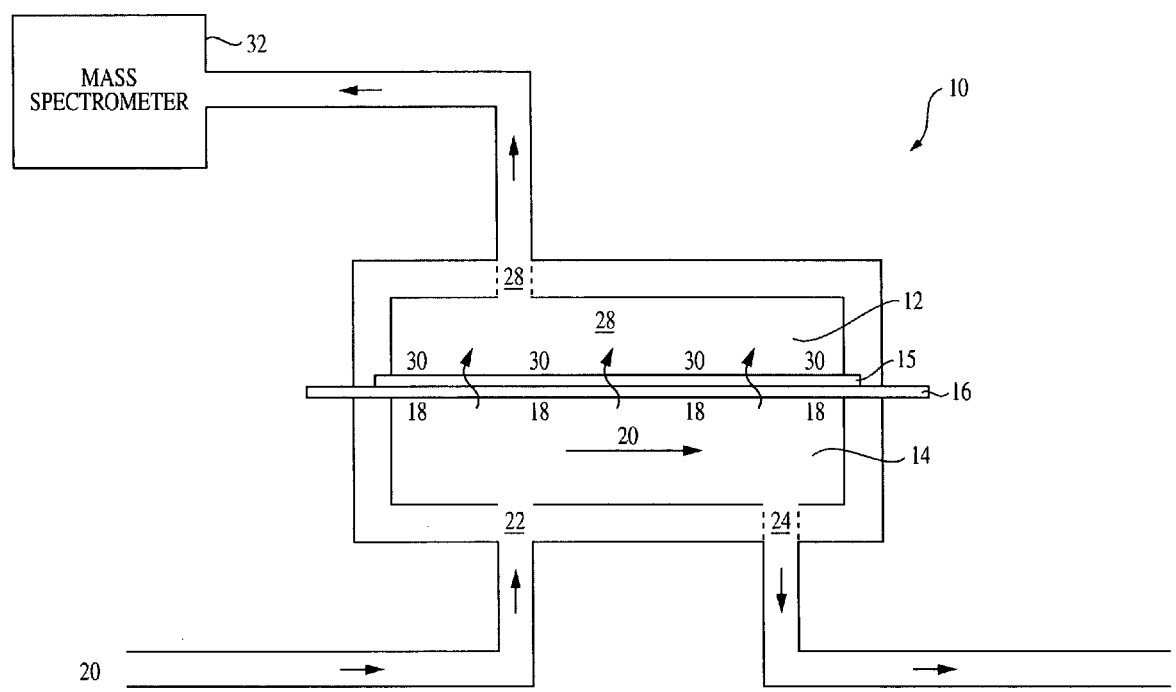
FIG. 1 shows a diagram of a test chamber for measuring the gas transmission rate of a guard material.

FIG. 1 illustrates the test setup for conducting the first step of the method in accordance with the present invention. A test chamber 10 includes an upper diffusion cell 12 and a lower diffusion cell 14. A guard material 16 is positioned on top of the lower diffusion cell 14 and a support grid 15 is positioned on top of the guard material. The upper and lower diffusion cells 12 and 14 are then clamped together with support grid 15 and guard material 16 therebetween. It is desirable, but not essential, for the guard material 16 to have a certain rigidity so that it does not deform under the high-vacuum system of the mass spectrometer but the guard material should not be so rigid or brittle that it fractures. Polyester materials such as polyethylene terephthalate (e.g. MYLAR® available from Dupont, Wilmington, Del.); polystyrenes such as acrylonitrile butauliene styrene; and polycarbonate materials such as GE Plastics™ and LEXAN® may be used. In the alternative, it is not essential that the guard material have any rigidity because the support grid 15, disclosed in further detail below, lends support to the guard material so that deformation does not occur. Therefore, any film forming material may be used as the guard material so long as it has a high gas transmission rate. For purposes of the present invention, guard materials having a transmission rate in the range of 0–500 cc/m²-day are considered to be low transmission rate materials. High transmission rate materials are defined as those materials which permit the passage of molecules at transmission rates in excess of 500 cc/m²-day. While any high transmission rate material may be used as the guard material in accordance with the present invention, ideally, the guard material preferably will have a gas transmission rate that is about one hundred times greater than the gas transmission rate of the test material so that it is not a permeation barrier for the test gas. For example when measuring the gas transmission rate of helium, polyethylene terephthalate, available as MYLAR® from Dupont, has both the requisite rigidity and a transmission rate of 1000 cc/m²-day and provides an excellent guard material. Guard materials used in accordance with the present invention will preferably be approximately 5 mil in thickness but may vary depending on the size of the test chamber 10 and, the gas transmission rate of the test material.

A support grid 15 is also used in accordance with the present invention. The function of the support grid 15 is to support the guard material 16 when there is a delta pressure caused by the high vacuum conditions associated with the upper diffusion cell. The support grid 15 may be made from any material that does not impede the diffusion rate of the test gas and is typically made from sintered metal, i.e. porous stainless steel.

The lower diffusion cell 14 has a gas inlet 22 and a gas outlet 24. A source of the test gas 20, the transmission rate of which is being calculated, is introduced through the gas inlet 22 to the lower diffusion cell 14 at a flow rate of approximately 10 cc per minute creating a high gas concentration side 18 in the lower diffusion cell 14. The upper diffusion cell 12 is subject to the high-vacuum system of the mass spectrometer 32. However, it must be emphasized that the total pressure of the system, i.e. the vacuum in the upper diffusion cell, does not affect the permeation rate of the guard material 16. Rather, the molecules of the test gas diffuse through the guard material because of the concentration gradient that exists in the lower diffusion cell 14 and the upper diffusion cell 12. Because no gas is present in the upper diffusion cell 12, a "low" gas concentration exists. The high gas concentration in the lower diffusion cell 14, causes a "high" gas concentration across the test material and, therefore, diffusion. Again, the support grid 15 being porous does not impede the diffusion of the test gas 20.

The test gas 20 flows generally through the lower diffusion cell 14 and is exhausted out the gas outlet 24. The test gas 20 is sorbed at the entering face (high concentration side) 18 of the guard material 16. The dissolved penetrant molecules of the test gas 20 diffuse through the polymeric structure of the guard material 16 and desorb at the exit face 30 of the guard material (low concentration side) through the support grid 15 and into the upper diffusion cell 12 and the high-vacuum system 28 created by the mass spectrometer 32. The test gas molecules enter the mass spectrometer and the gas transmission rate of the guard material is then calculated ($TR_1$). If the guard material 16 has the requisite rigidity as discussed previously, it does not deform or fracture in the presence of the high-vacuum system 28. In the alternative, if the guard material 16 does not have rigidity and one relies on the support grid 15 to prevent deformation or if the guard material does have rigidity it will also protected from delta pressures caused by the vacuum, i.e. force caused by changes in pressure. One skilled in the art will appreciate that in the test chamber depicted in FIGS. 1–3 and 5 an optional O-ring can be placed on the outer or inner surface of the lower diffusion cell to provide a better seal when the lower and upper diffusion cells are closed.

Figure 2:
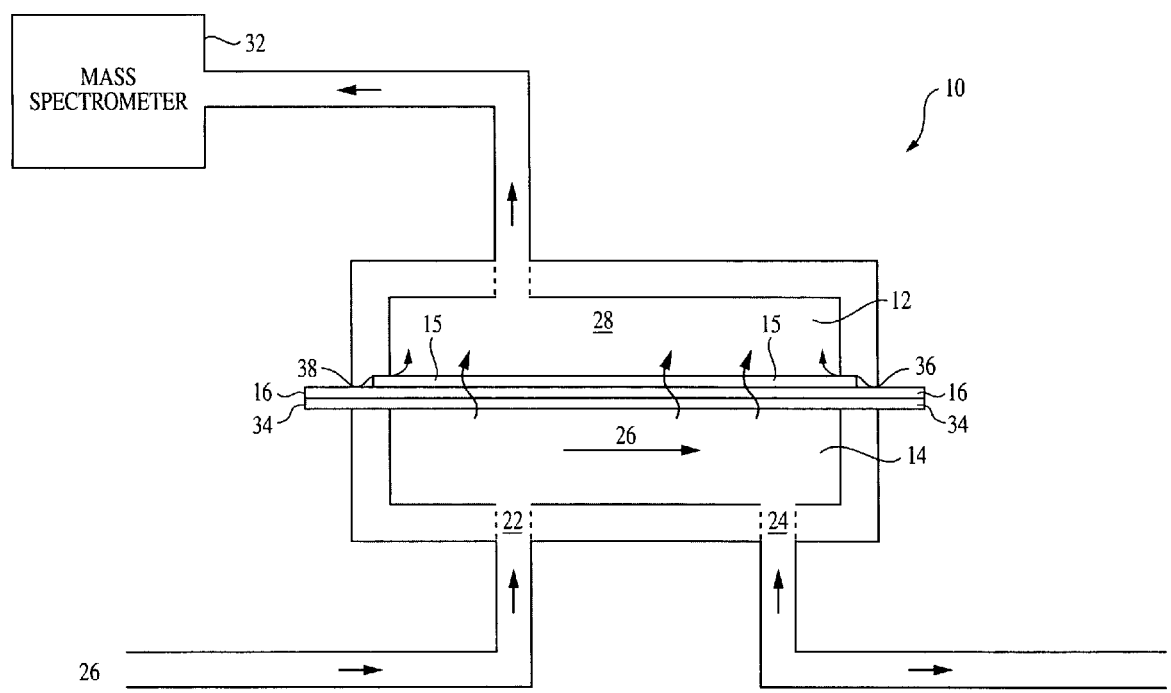
FIG. 2 shows a diagram of a test chamber for calculating the leak rate of a test chamber wall seals and measuring the gas transmission rate through the combination of a test material sample and a guard material.

FIG. 2 illustrates the second step of the method in accordance with the present invention, calculating the leak rate of the chamber wall seals 36, 38. As noted previously, it is only necessary to perform the second test when the test gas is present in air. If the test gas is not present in air, the measurement will be negligible and the second step can be eliminated.

Referring to FIG. 2, we assume that the test gas is present in air and conduct a baseline test to determine the leak rate of chamber seals, 36 and 38. As can be seen, the test cell setup is identical to that illustrated in FIG. 1 with the exception that a test material sample 34 is introduced into the test chamber. The test material sample is positioned over and immediately adjacent the lower diffusion cell 14. The guard material 16 is positioned over the test material sample 34, and the support grid 15 is positioned over the guard material and immediately adjacent the upper diffusion cell 12. The three materials are clamped between the upper and lower diffusion cells 12 and 14, respectively. It will be appreciated that the guard material 16 acts to support the test material sample 34 from deforming in the case of elastomeric materials and/or delaminating or fracturing in the case of brittle materials as the guard material is subjected to the high-vacuum system 28 present in the upper diffusion cell 12. The support grid 15 in turn protects the guard material 15 from delta pressures in the upper diffusion cell 12 caused by the vacuum. When clamped together, the upper and lower diffusion cells 12, 14 form chamber seals 36, 38.

In the second step, a second gas 26 that is not sensed by the mass spectrometer is introduced into the lower diffusion cell 14 at a rate of approximately 10 cc per minute. Those skilled in the art will appreciate that any gas may be introduced into the lower diffusion cell 14 in this second step so long as it is different than the test gas 20 and, therefore, not detectable by the mass spectrometer 32. A non-limiting list of gases that may be used include helium, hydrogen, nitrogen, argon, xenon, krypton, carbon dioxide and oxygen. As second gas 26 is introduced through inlet 22 into the lower diffusion cell 14 it flows generally through the lower diffusion cell 14 and is exhausted out gas outlet 24. Again, second gas 26 establishes a high concentration side in the lower diffusion cell 14 and because no gas is present in the upper diffusion cell 12, the upper diffusion cell 12 establishes the low concentration side of the test chamber.

Second gas 26 is sorbed at the entering face (the high concentration side) of the test sample material 34. The dissolved penetrant molecules of the inert gas diffuse first through the test material sample 34 and then through the guard material 16 and desorb at the exit face (the low concentration side) of the guard material 16 through the support grid 15 and into the upper diffusion cell 12. However, second gas 26 is not capable of being measured because the mass spectrometer is tuned to the test gas, which is not present. To the extent the chamber walls 36, 38 leak and the test gas is present in air, the mass spectrometer will detect any test gas that leaks through chamber wall seals 36, 38. The leak rate of the chamber wall seals 36, 37 can then be determined. It will be appreciated by those skilled in the art that if the test gas is not present in air then this second step may be eliminated.

Figure 3:
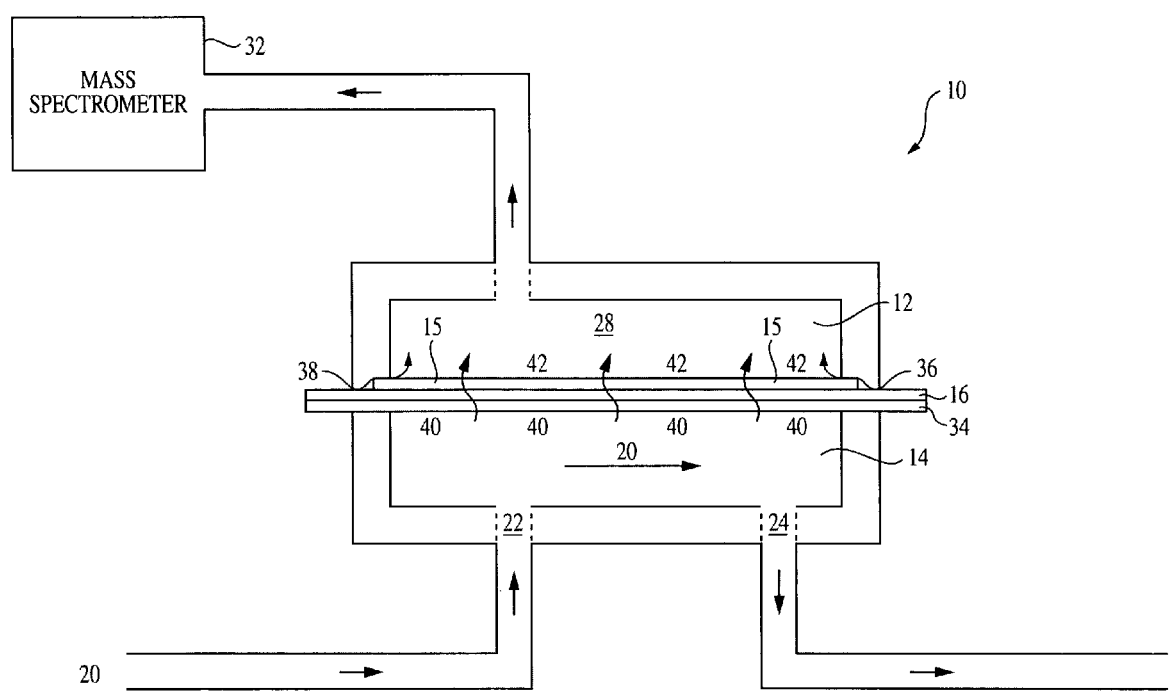
FIG. 3 shows a diagram of a test chamber for measuring the gas transmission rate of a test sample material in combination with a guard material.

Referring to FIG. 3 the test chamber used in the third step of the present invention is illustrated. In the third step the gas transmission raze of the combined guard material 16 and test material sample 34 are measured. Again, it will be appreciated that the guard material 16 acts to support the test material sample 34 from deforming in the case of elastomeric materials and/or delaminating or fracturing in the case of brittle materials because the guard material 16 is exposed to the high-vacuum system 28 in the upper diffusion cell 12 and not the test material sample 34. In addition, it will be appreciated that the setup for the third test is identical as the second step except tat the test gas 20 is once again used instead of the second gas 26. Porous support grid 15 is again used to protect the guard material 16 from delta pressures in the upper diffusion cell.

In the third step in accordance with the present invention, the combined gas transmission rate of the test material sample and the guard material are measured. In the third step of the present invention, the test gas 20 is introduced into the lower diffusion cell 14 through the gas inlet 22 at a flow rate of approximately 10 cc per minute where it flows generally throughout the lower diffusion cell 14 and exits through gas outlet 24. The lower diffusion cell 14 with the test gas 20 establishes the high concentration side of the test chamber. The test gas 20 is sorbed at the entering face of the test material sample 40 (the high concentration side) and dissolves into the polymeric structure of the test material sample 34. The dissolved penetrant molecules diffuse first through the test material sample 34 and then through the guard material 16 and desorb at the exit face 42 (the low concentration side) into the upper diffusion cell 12. The mass spectrometer 32 is tuned to the test gas 20. The gas transmission rate of the combined test material sample and guard material is then calculated ($TR_3$).

From these three measurements, the gas transmission rate of the test material sample may be calculated according to the following equation where $TR_1$ = Transmission rate of Guard material $TR_2$ = Transmission rate of Chamber Wall Seals $TR_3$ = Transmission rate of Guard material and Test Material Sample $$\frac{1}{(TR_3 - TR_2)} - \frac{1}{TR_1} = \frac{1}{TR_{TMS}}$$

Solving for $TR_{TMS}$ $$TR_{TMS} = \frac{(TR_3 - TR_2)(TR_1)}{(TR_1) - (TR_3 - TR_2)}$$

When the test is not present in air, $TR_2$ can be eliminated. The equation simplifies to:

$$\frac{1}{TR_3} - \frac{1}{TR_1} = \frac{1}{TR_{TMS}}$$

Solving for $TR_{TMS}$ $$\frac{(TR_3)(TR_1)}{TR_1 - TR_3} = TR_{TMS}$$

Further, when the gas transmission rate of the guard material is about 100 times higher than the gas transmission rate of the test material, $TR_1$ will drop out of the equation and the equation becomes:

$$\frac{1}{TR_3} = \frac{1}{TR_{TMS}}$$

Figure 4:
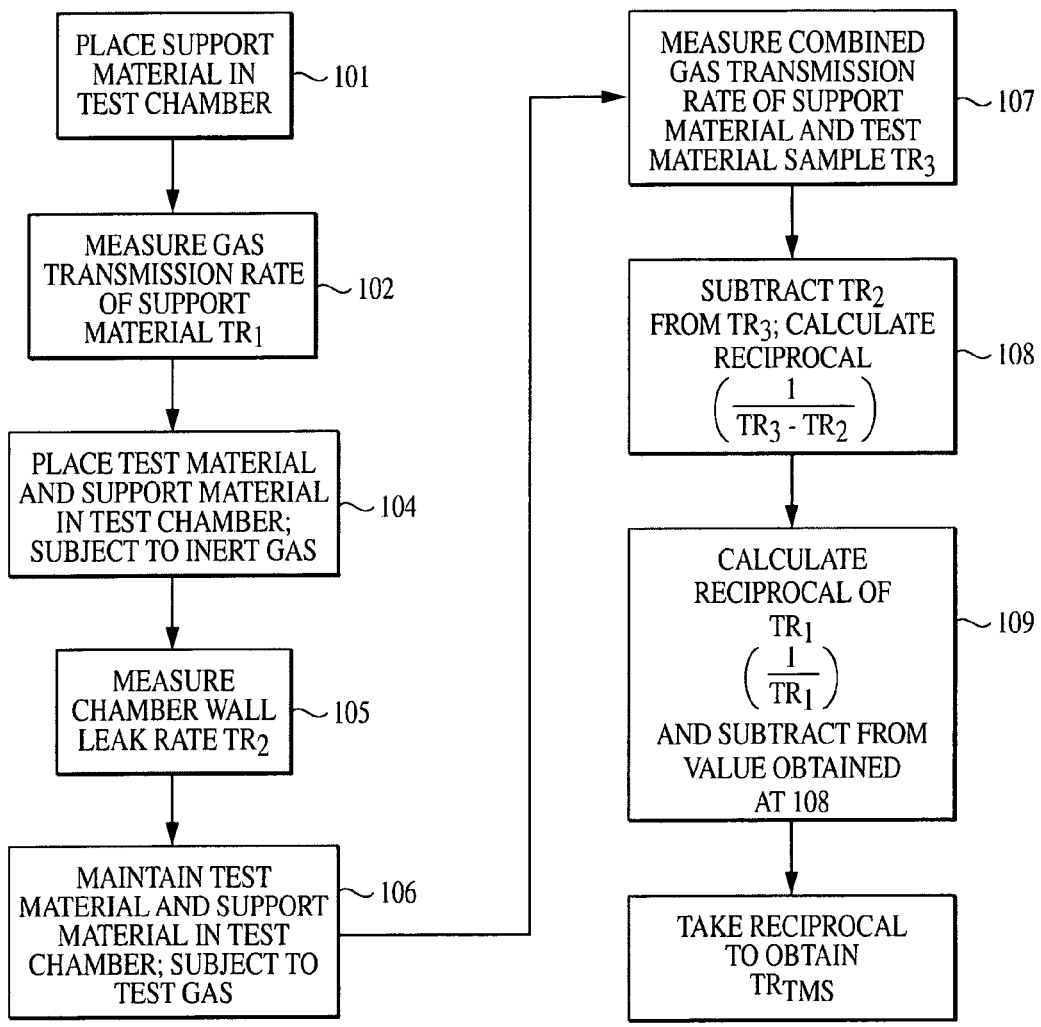
FIG. 4 shows a diagram of one process in accordance with the present invention.

Referring to FIG. 4, a flow diagram of the process described above, including the second test for determining the chamber wall leak rate, is illustrated. The second step may be eliminated under conditions discussed above. At step 101, the guard material is placed into the test chamber and is subjected to a test gas that flows through the lower diffusion cell 14 at a rate of approximately 10 cc per minute; a mass spectrometer creates high vacuum conditions in the upper diffusion cell 12; the test gas 20 sorbs at the entering face 18 (high concentration side) of the guard material 16, diffuses through the guard material, and desorbs at the exit face (low concentration side) of the guard material 16.

At step 102, the gas transmission rate of the guard material is measured.

At step 104, a test material sample 34 is positioned over and is immediately adjacent the lower diffusion cell 14 of the test chamber; the guard material 16 is placed over the test material sample 34 and a support grid 15 is placed over the guard material and is immediately adjacent the upper diffusion cell 12 of the test chamber; the upper and lower diffusion cells are clamped together to form chamber wall seals 36, 38; a second gas that the mass spectrometer cannot measure is introduced into the lower diffusion cell at an approximate rate of 10 cc per minute while the mass spectrometer creates a high-vacuum system in the upper diffusion cell 12.

At step 105, the leak rate of the chamber wall seals 36, 38 is measured.

At step 106, the guard material and test material sample are maintained in place; the test gas is again introduced into the lower diffusion cell at a rate of approximately 10 cc per minute and exhausted out the gas outlet; the upper diffusion cell is subjected to the high-vacuum system of the mass spectrometer; the test gas 20 is sorbed at the entering face 40 of the test material sample 34 and diffuses first into the polymeric structure of the test material sample and then through the guard material; the test gas desorbs at the exit face 42 of the guard material 16.

At step 107, the gas transmission rate of the combined guard material and test material sample is measured.

At step 108, the chamber wall leak rate is subtracted from the gas transmission rate of the guard material and the test material sample (i.e. $TR_3$–$TR_2$); the reciprocal is then calculated.

At step 109, the reciprocal of the gas transmission rate of the guard material ($TR_1$) as measured at step 101 is calculated and subtracted from the value obtained at step 108.

Finally, at step 110 the reciprocal value of the result obtained in step 109 is taken to reveal the test material transmission rate ($TR_{TMS}$).

Figure 5:
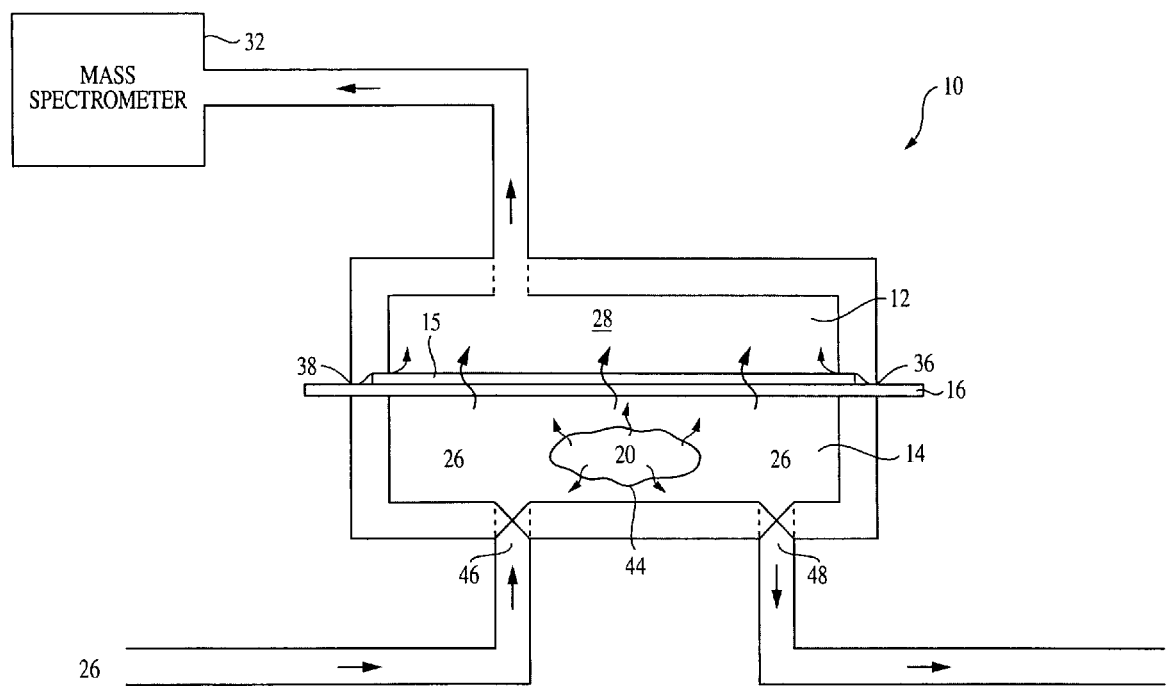
FIG. 5 shows a diagram of a test chamber for measuring the gas transmission rate of a sealed package.

Referring now to FIG. 5, the apparatus and process in accordance with the present invention is depicted for testing the gas transmission rates of sealed packages and the like. It is contemplated that the apparatus and process in accordance with the present invention may be used in a manufacturing setting to calculate the shelf life of certain products. For example, many types of athletic shoes such as NIKE®, ADIDAS® and SAUCONY® among others, include air bladders containing a gas in the lower support structure of the shoes to cushion the feet of runners, walkers, etc. who use them. As shoes are manufactured, a random sample of the air bladders may be obtained and allowed to equilibrate. After equilibrium is reached, the air bladder may be placed in the apparatus in accordance with the present invention, and the gas transmission rate of the bladder may be determined. Given the calculated gas transmission rate of the bladder, it can then be calculated what the expected shelf life of the air bladder and, therefore, the shoe will be. Depending on the value obtained, the sample bladder may or may not meet quality standards and the manufacturing process may be adjusted.

Similarly, the apparatus and process in accordance with the present invention may be used to test the gas transmission rates of food packaging. For example, a package containing potato chips or pretzels (or any food item) and a gas contained within the package, which preserves food characteristics such as flavor, crispness, etc. may be placed in the apparatus in accordance with the present invention. As the packaged items are manufactured, a random sample of the packages may be obtained and allowed to equilibrate. After equilibrium is reached, the package may be placed in the apparatus in accordance with the present invention, and the gas transmission rate of the package may be determined.

Given the calculated gas transmission rate of the package, it can then be calculated what the expected shelf life of the package will be. Depending on the value obtained, the packages from the particular production lot or batch may or may not meet quality standards and the manufacturing process, e.g., sealing operation, may be adjusted or new packaging materials may be considered.

Similarly, the method and apparatus in accordance with the present invention can be used for testing computer hard drives. It is desirable for a variety of reasons to include helium in the shell of the hard drive. The gas transmission rate of the shell which is sealed (typically with an epoxy), and the rate at which the helium will leak out of the hard drive, directly affects the shelf-life of the hard drive. Using the apparatus and method in accordance with the present invention, the gas transmission rate of a random sampling of hard drives may be determined. As with any item that contains a gas, the hard drives need to equilibrate after they come off the production line. After equilibration, the hard drive is placed in the apparatus of the present invention and the gas transmission rate of the gas contained within the shell is calculated in accordance with the method of the present invention. Depending on the value obtained, one can then calculate the expected shelf life of the hard drive. If the expected shelf life falls short of quality standards, the particular seal being used may be changed or the manufacturing process may be adjusted.

Referring to FIG. 5, in operation a sealed package, bladder, hard drive or any manufactured item 44 containing a test gas 20 is placed in the lower diffusion chamber 14 of the apparatus 10 in accordance with the present invention. It should be noted that the apparatus is identical to the apparatus of FIG. 1 with the exception that gas inlet valve 46 and gas outlet valve 48 are substituted for gas inlet 22 and gas outlet 24. Gas outlet valve 48 is in the on position and gas inlet valve 46 is in the open position white gas 26 is pumped into lower diffusion chamber 14. It is desirable to flush the test chamber with three to live times the volume of the test chamber. Alter flushing diffusion cell 14 tar several minutes, both valves are closed. The test gas 20 contained within package 44 diffuses from the high gas concentration side of the test chamber across the package membrane, the guard material and the support grid, which is completely porous and does not binder diffusion to the low gas concentration side. It is important to note that both gas 20 and gas 26 diffuse across the guard material and support grid. however, because the mass spectrometer is tuned to the test gas 20, gas 26 is not measured. The gas transmission rate of the sealed package is then calculated using the formula above. If a guard material is being used that baa a gas transmission rate of less than about one hundred times the gas transmission rate of the sealed package material (the test material), those skilled in the art will appreciate that the test to measure the gas transmission rate for the guard material, as described above, should be included in operation and in the calculation.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

We claim:

1. A method for measuring the gas transmission rate of a sealed manufactured package containing a test gas comprising:
  (a) providing a test chamber including an upper diffusion cell and a lower diffusion cell that when closed form a chamber wall seal, a gas valve inlet and a gas valve outlet in fluid communication with the lower diffusion cell and a mass spectrometer in communication with the upper diffusion cell;
  (b) placing a sealed package containing a test gas in the lower diffusion cell;
  (c) selecting a guard material of a known type and positioning said guard material between the lower diffusion cell and the upper diffusion cell;
  (d) positioning a support grid over the guard material and immediately adjacent the upper diffusion cell;
  (e) closing the upper and lower diffusion cells;
  (f) opening said gas inlet valve and said gas outlet valve;
  (g) providing through said gas inlet valve and out said gas outlet valve a source of a second gas different than the test gas to flush the lower diffusion chamber;
  (h) closing said gas inlet and gas outlet valve;
  (i) operating a mass spectrometer thereby creating a high-vacuum system in the upper diffusion cell; and
  (j) measuring the gas transmission rate of the sealed package;

wherein the guard material has a high gas transmission rate relative to the gas transmission rate of the sealed package and wherein the gas transmission rate of the sealed package is calculated by calculating the reciprocal of the gas transmission rate of the sealed package.

* * * * *